United States Patent
Merchant et al.

(10) Patent No.: US 12,169,168 B2
(45) Date of Patent: Dec. 17, 2024

(54) SYSTEMS AND METHODS FOR EFFICIENT DETECTION OF HAZARDOUS FUEL GAS LEAKAGE WITHIN A GAS TURBINE COMPARTMENT

(71) Applicant: General Electric Company, Schenectady, NY (US)

(72) Inventors: Laxmikant Merchant, Karnataka (IN); Abhishek Mishra, Karnataka (IN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 231 days.

(21) Appl. No.: 17/661,461

(22) Filed: Apr. 29, 2022

(65) Prior Publication Data

US 2022/0357249 A1    Nov. 10, 2022

(30) Foreign Application Priority Data

May 4, 2021    (IN) .............................. 202111020382

(51) Int. Cl.
*G01N 1/38*    (2006.01)
*G01M 3/02*    (2006.01)

(52) U.S. Cl.
CPC .............. *G01N 1/38* (2013.01); *G01M 3/025* (2013.01)

(58) Field of Classification Search
CPC .... G01N 1/38; G01N 33/0011; F01D 21/003; F01D 25/30; G01M 3/002; G01M 3/222; G01M 15/14; G01M 3/02
See application file for complete search history.

(56) References Cited

U.S. PATENT DOCUMENTS

| | | | |
|---|---|---|---|
| 8,061,890 B2 | 11/2011 | Suhner | |
| 2002/0020232 A1* | 2/2002 | Yamagishi | G01N 15/0618 73/863.11 |
| 2010/0110826 A1 | 5/2010 | D'herde | |
| 2013/0104531 A1* | 5/2013 | Cho | F01N 3/24 60/302 |
| 2014/0080403 A1 | 3/2014 | Erickson et al. | |
| 2015/0000292 A1* | 1/2015 | Subramaniyan | F02K 1/48 60/39.12 |
| 2015/0000392 A1 | 1/2015 | Knestel et al. | |
| 2015/0226129 A1 | 8/2015 | Byrd et al. | |
| 2015/0308915 A1 | 10/2015 | Konatham et al. | |
| 2017/0130607 A1 | 5/2017 | Zhang et al. | |
| 2017/0328805 A1 | 11/2017 | Bermudez et al. | |
| 2018/0058972 A1 | 3/2018 | Zhang et al. | |
| 2018/0080846 A1 | 3/2018 | Zhang et al. | |
| 2020/0173366 A1 | 6/2020 | Akana et al. | |

FOREIGN PATENT DOCUMENTS

| | | |
|---|---|---|
| CN | 202647773 U | 1/2013 |
| EP | 0594657 B1 | 11/1996 |
| EP | 2686530 A1 | 1/2014 |
| WO | 2012/176127 A1 | 12/2012 |

* cited by examiner

*Primary Examiner* — David Z Huang
(74) *Attorney, Agent, or Firm* — Eversheds Sutherland (US) LLP (57) ABSTRACT

The present application provides a hazardous gas detection system to determine hazardous gas concentrations and/or temperatures within a flow of exhaust air in an exhaust duct of a gas turbine compartment. The hazardous gas detection system may include one or more sensors positioned within or in communication with the exhaust duct and a static mixer positioned upstream of the one or more sensors to promote mixing of the flow of exhaust air.

18 Claims, 8 Drawing Sheets

SYSTEMS AND METHODS FOR EFFICIENT DETECTION OF HAZARDOUS FUEL GAS LEAKAGE WITHIN A GAS TURBINE COMPARTMENT

CROSS-REFERENCE TO RELATED APPLICATIONS

This application claims priority pursuant to 35 U.S.C. 119(a) to India Patent Application No. 202111020382, filed May 4, 2021, which application is incorporated herein by reference in its entirety.

TECHNICAL FIELD

The present application and the resultant patent relate generally to gas turbine engines and more particularly relate to improved systems and methods for efficient detection of fuel gas leakage within a gas turbine compartment through the use of a static mixer to promote uniform gas concentrations and temperatures at the hazardous gas sensors.

BACKGROUND

Gas turbine engines and their related components and systems are often at least partially disposed within a compartment or other type of enclosure. Generally described, the gas turbine compartment protects the gas turbine engine from local environmental conditions, reduces acoustic emissions from the gas turbine engine, and insulates the immediate surroundings from heat emanating from the gas turbine engine during operation.

A hazardous gas detection system may be deployed within and/or proximate to the gas turbine compartment. The hazardous gas detection system may use gas sensors to detect or measure hazardous gas concentrations within the exhaust air leaving the compartment via a ventilation exhaust duct. The concentrations of hazardous gases, however, may be highly stratified within the ventilation exhaust duct. In other words, the concentration of the hazardous gases may not be uniform at the plane where the hazardous gas sensors are located due to the amount, location, and direction of leakage inside the compartment. There is therefore the potential that leaked fuel gas within the compartment may not be detected or may be detected with a lower explosive limit concentration ("LEL") lower than the actual concentration or vice versa by the hazardous gas sensors. There is a similar issue with respect to air temperature as the sensor readings may depend on the location of thermocouples within the ventilation exhaust duct.

For example, if the concentration of the hazardous gas reaches the lower explosive limit or reaches a predefined percentage of the lower explosive limit for the particular hazardous gas, the gas turbine engine must be shut down or tripped to address the leak. A false or anomalous reading may result in an unnecessary shut down of the gas turbine engine at the expense of gas turbine life, power availability, and/or loss of income that may result due to taking the power plant off line. There is thus a desire for an improved hazardous gas detection systems and methods. Such systems and methods may improve overall reliability and availability of the gas turbine engine by preventing false alarms and/or controlled shut downs or trips of the gas turbine engine.

SUMMARY

The present application and the resultant patent thus provide a hazardous gas detection system to determine hazardous gas concentrations and temperatures within a flow of exhaust air in an exhaust duct of a gas turbine compartment. The hazardous gas detection system may include one or more sensors positioned within or in communication with the exhaust duct and a static mixer positioned upstream of the one or more sensors to promote mixing of the flow of exhaust air.

The present application and the resultant patent further provide a method of determining a concentration or temperature of a hazardous gas in a flow of exhaust air in an exhaust duct of a gas turbine compartment. The method may include the steps of pulling the flow of exhaust air into the exhaust duct, positioning a static mixer in the flow of exhaust air, uniformly mixing the hazardous gas within the flow of exhaust air, and sensing the concentration of the hazardous gas.

The present application and the resultant patent further provide a hazardous gas detection system to determine hazardous gas concentrations and temperatures within a flow of exhaust air in an exhaust duct of a gas turbine compartment. The hazardous gas detection system may include one or more gas sensors and one or more temperature sensors positioned within or in communication with the exhaust duct and a static mixer positioned upstream of the one or more gas sensors and the one or more temperature sensors to promote mixing of the flow of exhaust air.

These and other features and improvements of the present application and the resultant patent will become apparent to one of ordinary skill in the art upon review of the following detailed description when taken in conjunction with the several drawings and the appended claims.

DETAILED DESCRIPTION

Figure 1:
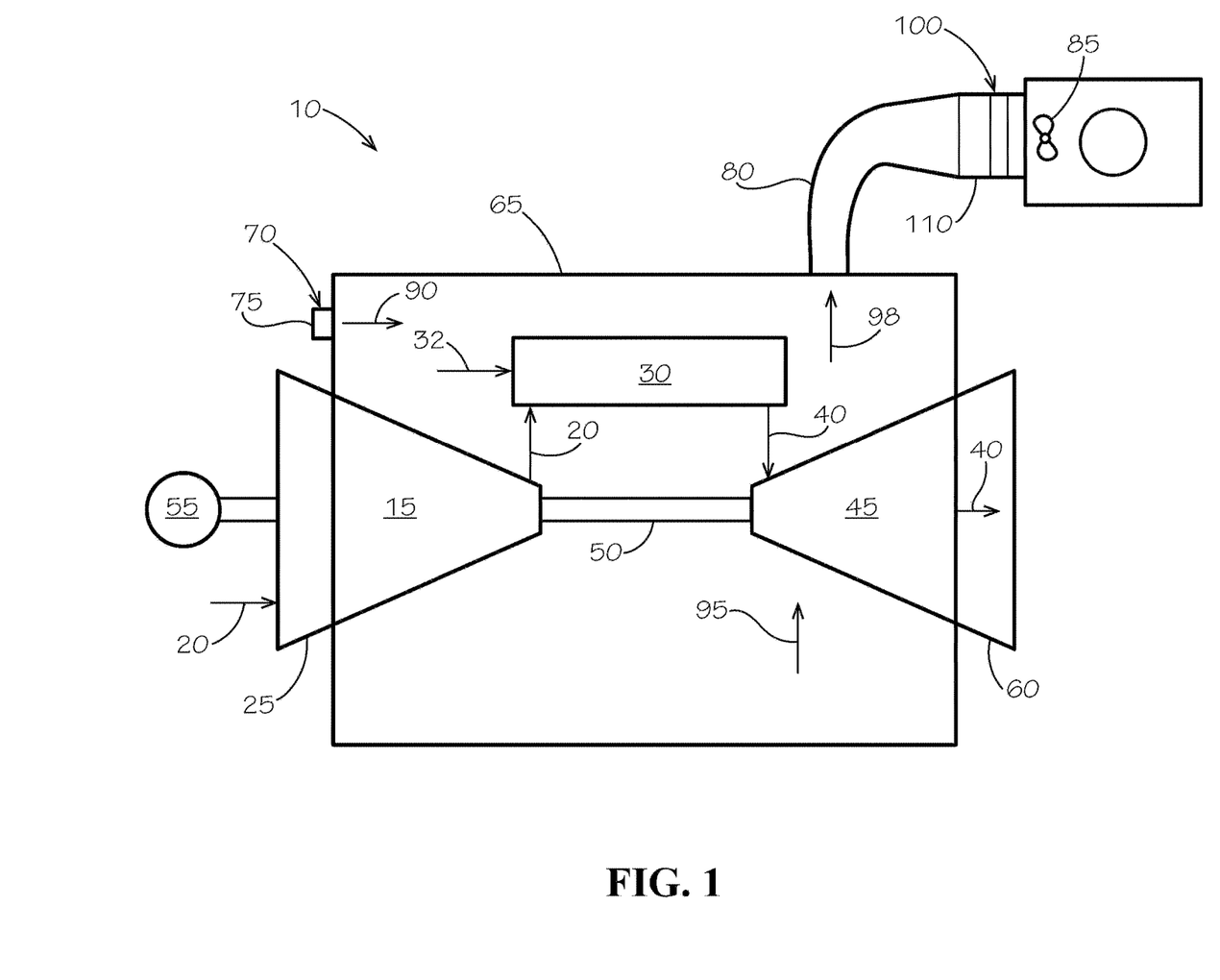
FIG. 1 is a schematic diagram of an exemplary gas turbine engine positioned within a gas turbine compartment with a ventilation exhaust duct having a hazardous gas detection system.

Referring now to the drawings, in which like numerals refer to like elements throughout the several views, FIG. 1 shows a schematic diagram of gas turbine engine 10 as may be used herein. The gas turbine engine 10 may include a compressor 15. The compressor 15 compresses an incoming flow of air 20 via an inlet section 25. The compressor 15 delivers the compressed flow of air 20 to a number of combustor cans 30. The combustor cans 30 mix the compressed flow of air 20 with a pressurized flow of fuel 32 and ignite the mixture to create a flow of hot combustion gases 40. Although only a single combustor can 30 is shown, the gas turbine engine 10 may include any number of combustor cans 30 positioned in a circumferential array and the like. The flow of the hot combustion gases 40 is in turn delivered to a turbine 45. The flow of the hot combustion gases 40 drives the turbine 45 so as to produce mechanical work. The mechanical work produced in the turbine 45 drives the compressor 15 via a shaft 50 and an electrical generator 55 or other type of an external load and the like. The hot combustion gases 40 may exit the gas turbine engine 10 via an exhaust section 60 and the like.

The gas turbine engine 10 may use natural gas, various types of syngas, liquid fuels, and/or other types of fuels and blends thereof. The gas turbine engine 10 may be any one of a number of different gas turbine engines offered by General Electric Company of Schenectady, New York, including, but not limited to, those such as a 7 or a 9 series heavy duty gas turbine engine and the like. The gas turbine engine 10 may have different configurations and may use other types of components. Other types of gas turbine engines also may be used herein. Multiple gas turbine engines, other types of turbines, and other types of power generation equipment also may be used herein together.

The gas turbine engine 10 may be at least partially enclosed within a gas turbine compartment 65. The gas turbine compartment 65 may have any suitable size, shape, or configuration. The gas turbine compartment 65 may include a ventilation system 70. The ventilation system 70 may include at least one ventilation inlet duct 75, at least one ventilation exhaust duct 80, and one or more fans or blowers 85 for drawing ventilation air 90 into the ventilation inlet duct 75, through the gas turbine compartment 65, and out via the ventilation exhaust duct 80. The ventilation air 90 may provide cooling to the gas turbine engine 10. In the event that a fuel gas 95 or other types of hazardous gases leak from one or more fuel flanges or other types of fuel connections, the fuel gas 95 or other types of hazardous gases may mix with the ventilation air 90 and flow out of the gas turbine compartment 65 as exhaust air 98 via the ventilation exhaust duct 80 of the ventilation system 70. Other components and other configurations may be used herein.

Figure 2A:
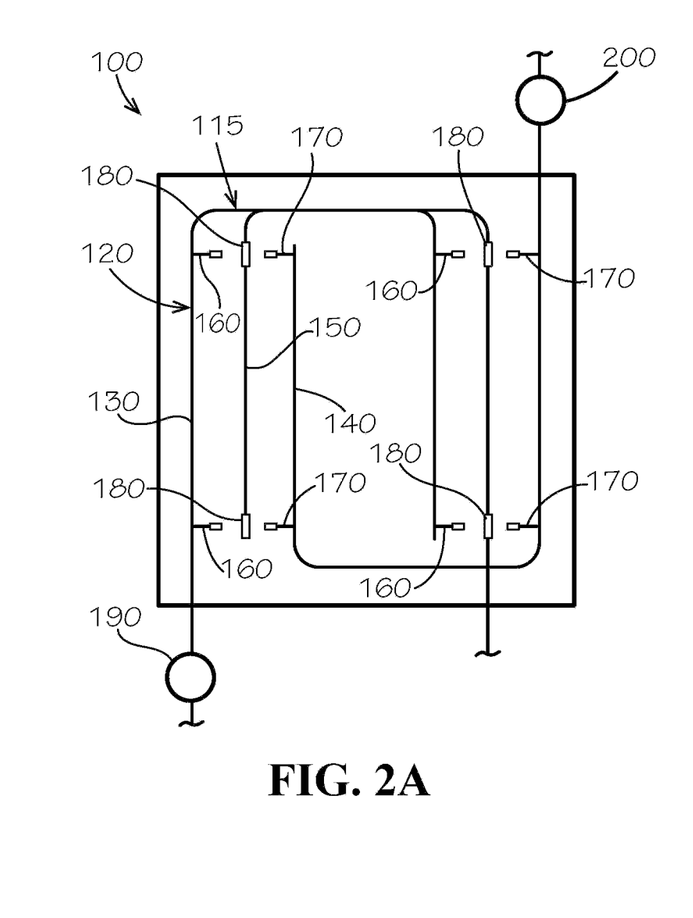
FIG. 2A is a schematic diagram of the hazardous gas detection system that may be used with the gas turbine compartment of FIG. 1.

FIG. 2A shows a hazardous gas detection system 100 as may be described herein. In this example, the hazardous gas detection system 100 may be positioned within an instrumentation duct 110 of the ventilation exhaust duct 80 (as shown in FIG. 1) or elsewhere. The hazardous gas detection system 100 is in the path of the exhaust air 98 flowing from the gas turbine compartment 65 via the ventilation exhaust duct 80.

The hazardous gas detection system 100 may include one or more sensors 115 on or in communication with one or more sampling tubes 120. In this example, a first air sampling tube 130, a second air sampling tube 140, and a temperature sampling tube 150 are shown. Any number or type of sampling tubes 120 may be used herein. Each of the sampling tubes 120 may have a substantial "U" shape and the like. The first air sampling tube 130 may have a number of first air sampling ports 160 positioned thereon. The second air sampling tube 140 may have a number of second air sampling ports 170. Four first air sampling ports 160 and four second air sampling ports 170 are shown, although any number may be used. The temperature sampling tube 150 may have a number of thermocouples 180 or other types of temperature sensors positioned thereon. Four thermocouples 180 are shown, although any number may be used. Other components and other configurations may be used herein.

The sampling tubes 120 may extend out of the instrumentation duct 110. The first air sampling tube 130 may be in communication with a first gas sensor 190. The second air sampling tube 140 may be in communication with a second gas sensor 200. The gas sensors 190, 200 may be infrared gas sensors and the like. The gas sensors 190, 200 may be configured to detect the concentration of certain hazardous gases in the flow of the exhaust air 98. Specifically, the exhaust air 98 may flow into the instrumentation duct 110, into the air sampling tubes 130, 140, and pass the gas sensors 190, 200. The gas sensors 190, 200 may be in communication with a controller (not shown) of the gas turbine engine 10 and/or a dedicated controller. The gas sensors 190, 200 may send signals corresponding to the gas concentration within the exhaust air 98 to the controller.

Likewise, the temperature tube 150 may extend out of the instrumentation duct 110. The exhaust air 98 may flow into the instrumentation duct 110 and pass the thermocouples 180 or other types of temperature sensors. The thermocouples 180 may be in communication with the controller of the gas turbine engine 10 and/or a dedicated controller. The thermocouples 180 may send signals corresponding to the temperature of the exhaust air 98 to the controller.

Figure 2B:
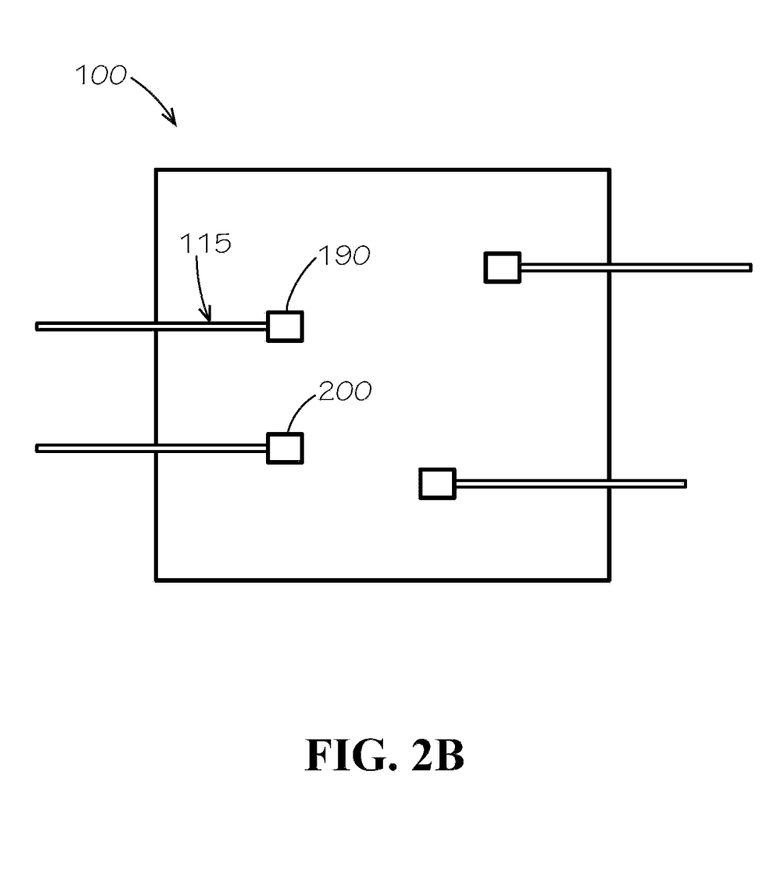
FIG. 2B is a schematic diagram of an alternative embodiment of the hazardous gas detection system that may be used with the gas turbine compartment of FIG. 1.

FIG. 2B shows a similar configuration of the instrumentation duct 110. As opposed to the grouped configuration of the sampling tubes 120 described above, the sensors 115 themselves may be in the flow of exhaust air 98. The sensors 115 may individually sense the concentrations or temperature of the flow of exhaust air 98. The sensors 115 may be in communication with the controller and the like. Any number of sensors 115 may be used herein.

As described above, gas concentrations and/or temperatures in the flow of the exhaust air 98 outside of predetermined ranges as detected by the hazardous gas detection system 100 may cause the controller to shut down the gas turbine engine 10. The concentrations and/or temperatures of the flow of the exhaust air 98, however, may be stratified. For example, different readings may be generated based upon the location of the leak in the gas turbine compartment 65, the direction of the leak, the magnitude of the leak, and the proximity of the leak to the sensors 190, 200 of the hazardous gas detection system 100.

Figure 3:
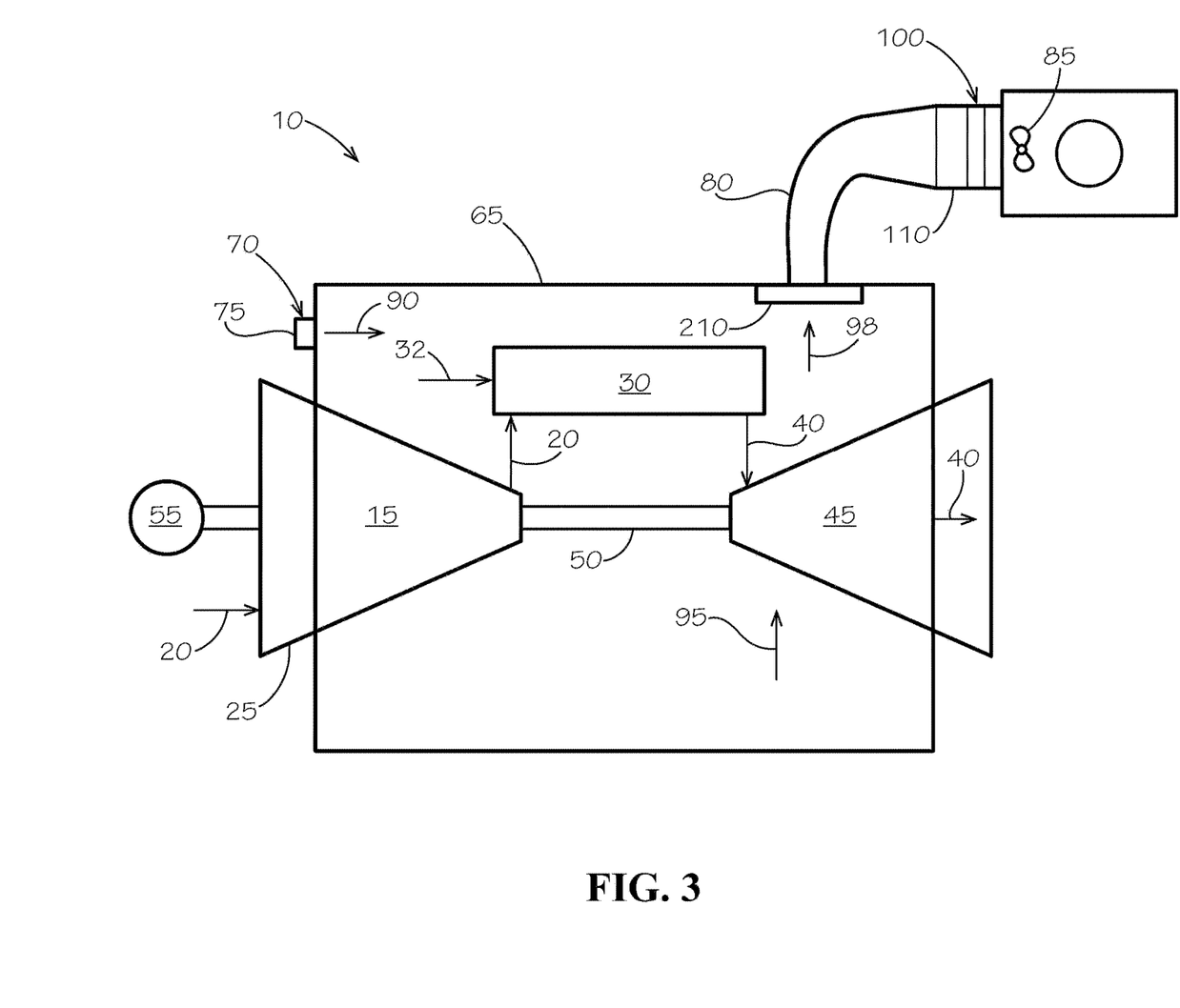
FIG. 3 is a schematic diagram of the gas turbine compartment and the ventilation exhaust duct with the hazardous gas detection system of FIG. 1 showing an example static mixer.
Figure 4:
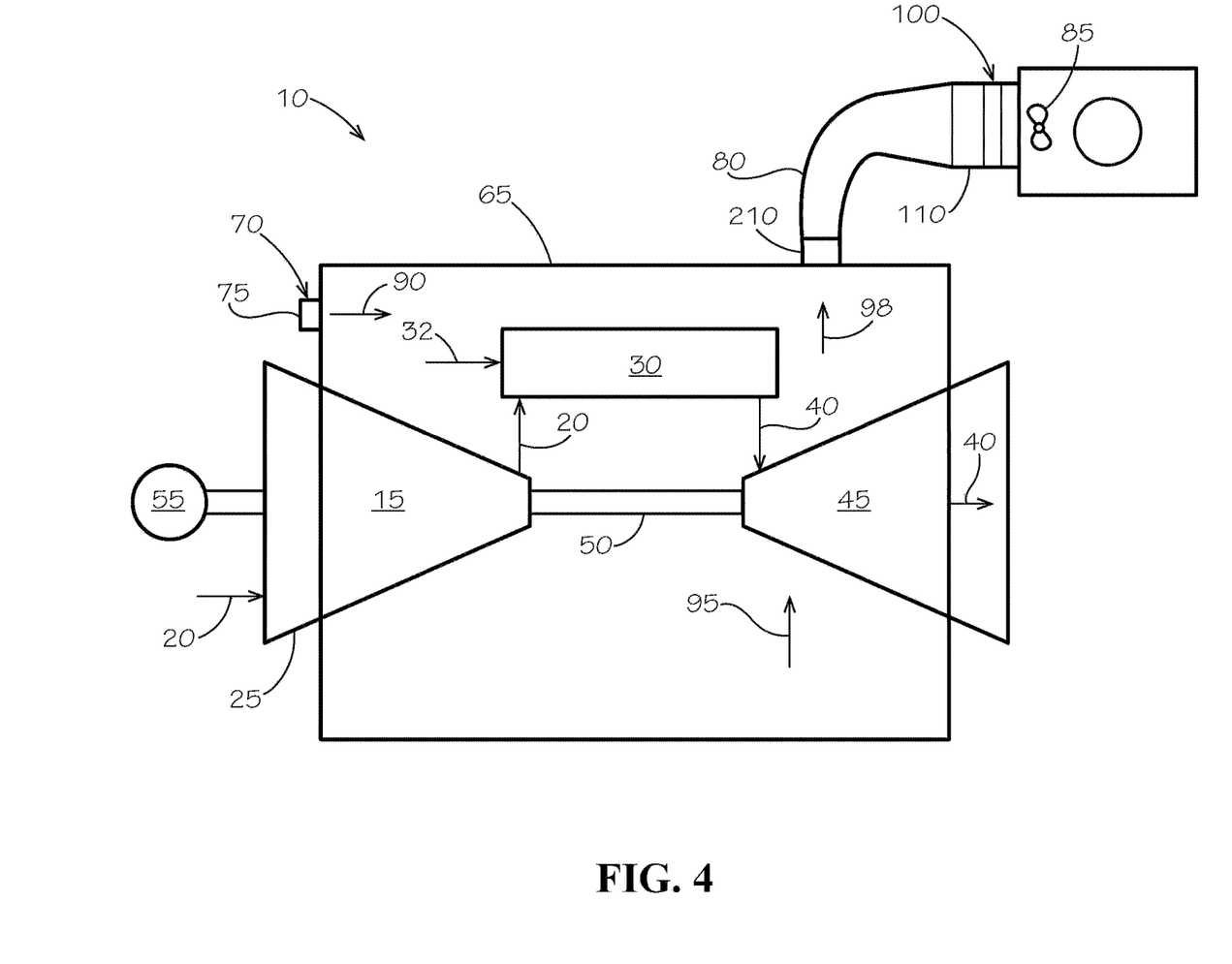
FIG. 4 is a schematic diagram of the gas turbine compartment and the ventilation exhaust duct with the hazardous gas detection system of FIG. 1 showing a further example of a static mixer.
Figure 5:
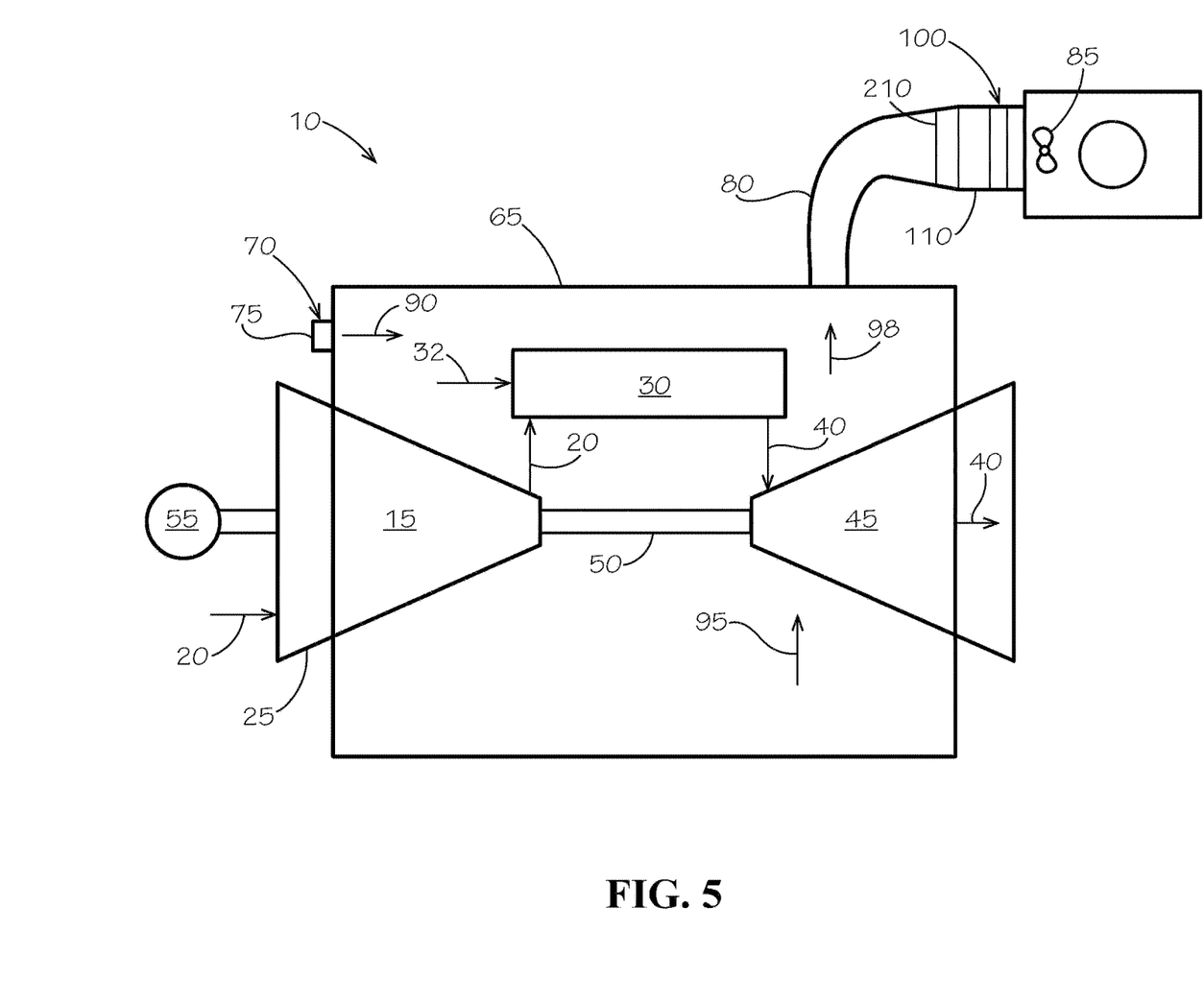
FIG. 5 is a schematic diagram of the gas turbine compartment and the ventilation exhaust duct with the hazardous gas detection system of FIG. 1 showing a further example of a static mixer.

The hazardous gas detection system 100 thus may include a static mixer 210 as shown in FIGS. 3-5. The static mixer 210 may be positioned within the flow path of the exhaust air 98 to produce a more uniform or homogenous mixture of the leaked fuel gas 95 and the ventilation air 90 upstream of the instrumentation duct 110. The more uniform or homogenous mixture of the exhaust air 98 allows the hazardous gas detection system 100 to detect the leaked fuel gas 95 more easily and with higher reliability. The static mixer 210 may be any type of two- or three-dimensional structure that promotes good mixing of the gases with a minimal pressure drop thereacross.

The static mixer 210 may have a number of different configurations and locations. For example, the static mixer 210 may be positioned within the gas turbine compartment 65 adjacent to the ventilation exhaust duct 80 as is shown in FIG. 3. Alternatively, the static mixer 210 may be positioned within the ventilation exhaust duct 80 adjacent to the gas turbine compartment 65 as is shown in FIG. 4. Likewise, the static mixer 210 may be positioned within the ventilation exhaust duct 80 adjacent to the instrumentation duct 110 as is shown in FIG. 5. Other locations and other configurations may be used herein.

Regardless of the position, the static mixer 210 will have a pressure drop thereacross to achieve good mixing. Given that the pressure drop is largely proportional to the square of the velocity of the exhaust air 98 therethrough, the position of the static mixer 210 within the gas turbine compartment 65 as is shown in FIG. 3 may have the lowest velocity and hence the lowest pressure drop. The velocity of the exhaust air 98 may increase as the flow enters the smaller ventilation exhaust duct 80 as is shown in FIG. 4 and may further increase as the flow extends to the instrumentation duct 110 as is shown in FIG. 5. Given such, the pressure drop will increase about the inlet of the ventilation air exhaust duct 80 and further increase about the instrumentation duct 110. The higher the pressure drop, the larger the fan 85 may be required in terms of static head rise capability. With the necessity for a higher static head capability, a more expensive fan 85 (in terms of size and operating expense) may be required.

Figure 6:
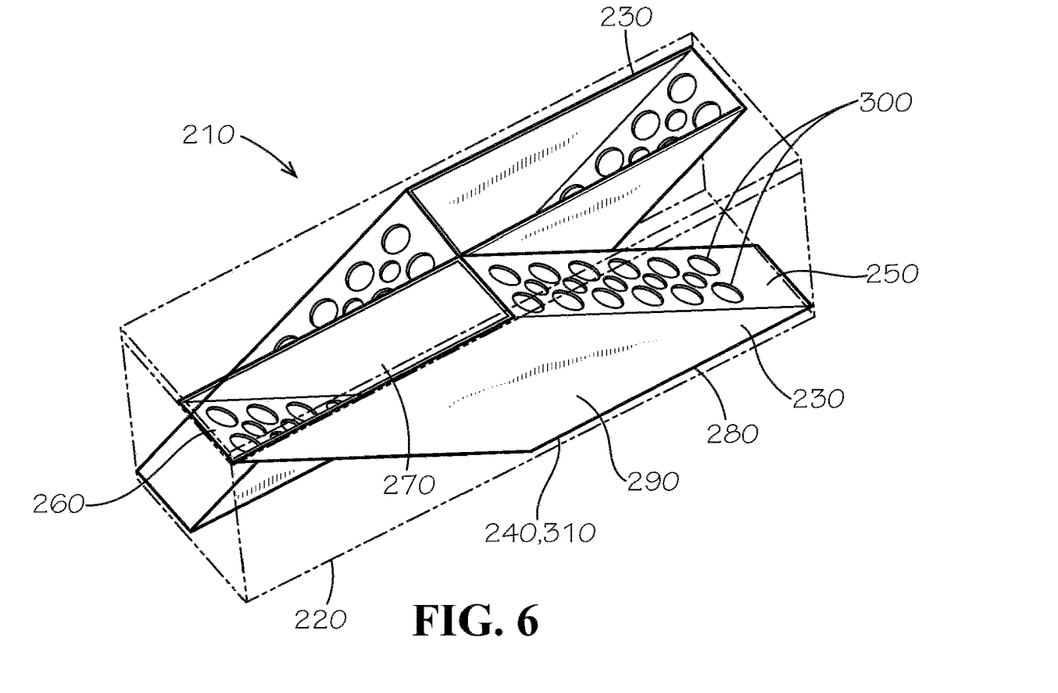
FIG. 6 is a perspective view of a static mixer that may be used with the hazardous gas detection system.

FIGS. 6-10 show different examples of the static mixers 210. In FIG. 6, the static mixer 210 may include an outer shell 220 and a pair of ducts 230. Each of the ducts 230 may have a largely rectangular shape 240 with a side entrance wall 250, a side exit wall 260, a pair of top walls 270, a pair of bottom walls 280, and a pair of lateral side walls 290. (The recited positions of top, bottom, and side are for respective orientation only. Any wall can be a top, bottom, or side depending upon orientation.) The side entrance wall 250 and the side exit wall 260 of each duct 230 may have a number of apertures 300 therein. The size and position of the apertures 300 may vary. The ducts 230 may be positioned in a crossed and offset configuration 310. Specifically, both the side entrance walls 250 and the side exit walls 260 may be offset from each other by about ninety degrees or so. Other angles may be used herein. The static mixer 210 may be made out of any type of material suitable for the high temperature environment of the gas turbine compartment 65 and the flow of exhaust air 98. Other components and other configurations may be used herein.

In use, the exhaust air 98 may enter the side entrance walls 250 of each duct 230 at an angle, turbulently mix therein, and exit via the side exit walls 260. The use of the apertures 290 further promotes the turbulence and mixing therein. The exhaust air 98 further continues to mix downstream of the static mixer 210 until a substantially homogenous flow or a more homogenous flow reaches the instrumentation duct 110 and the sampling tubes 120.

Figure 7:
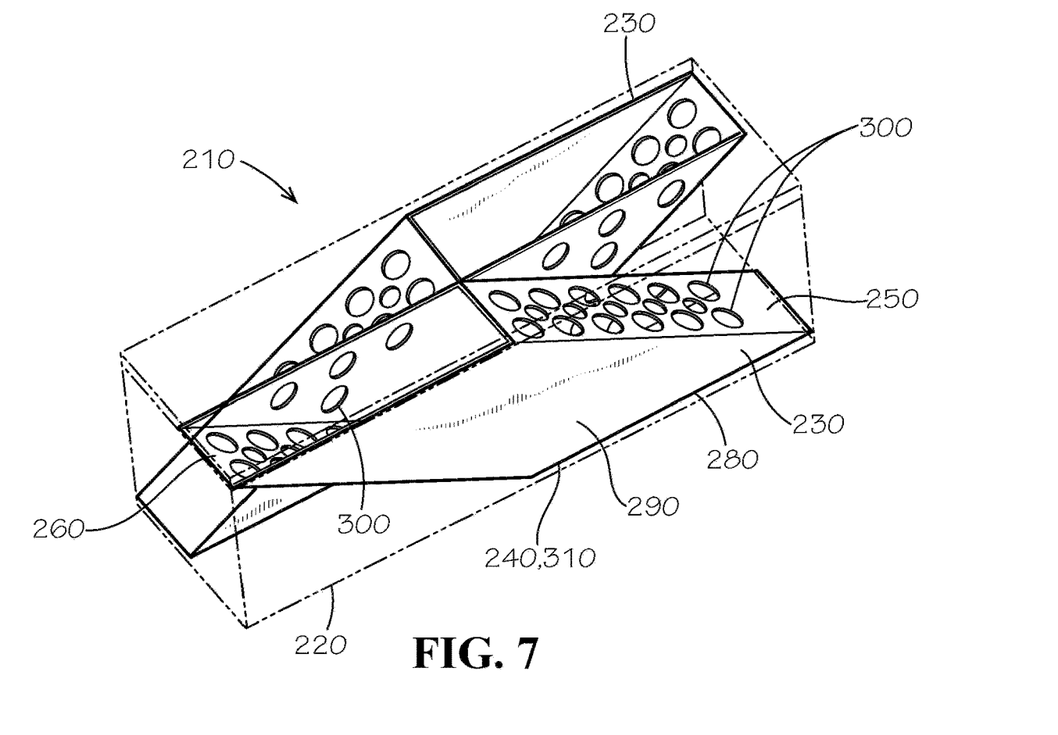
FIG. 7 is a perspective view of a further example of a static mixer that may be used with the hazardous gas detection system.
Figure 8:
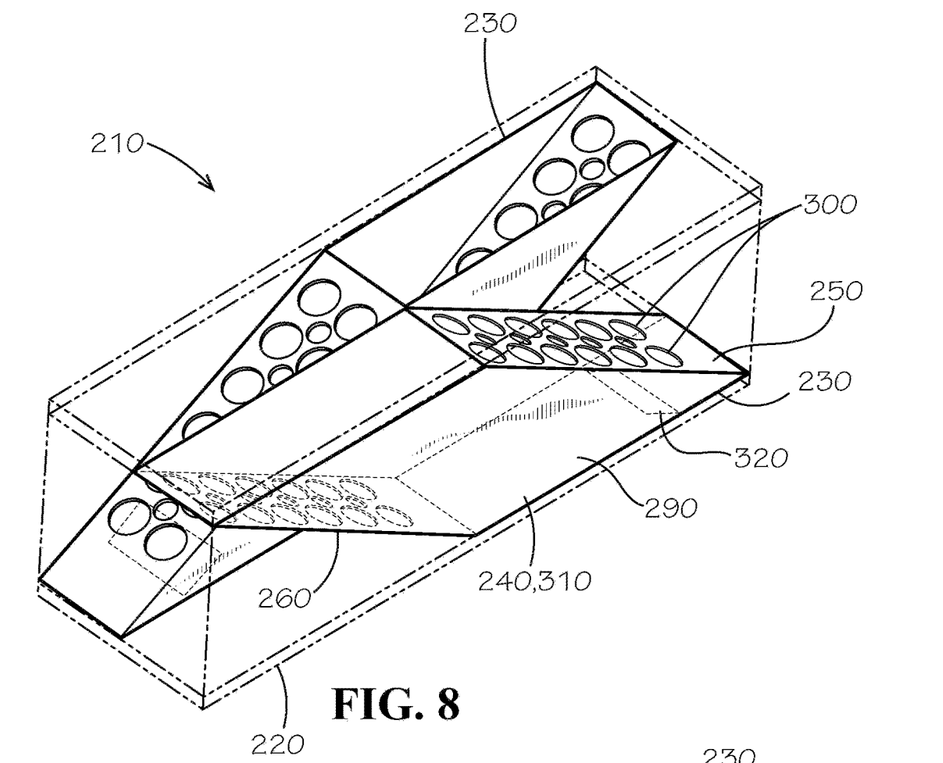
FIG. 8 is a perspective view of a further example of a static mixer that may be used with the hazardous gas detection system.

FIG. 7 shows a similar example of a static mixer 210 with the addition of apertures 300 positioned within the adjoining lateral sidewalls 290. These lateral apertures further promote lateral mixing between the ducts 230. FIG. 8 shows a further example of a static mixer 210 with an internal splitter plate 320. The splitter plate 320 further promotes mixing through the ducts 230. Other components and other configurations may be used herein.

Figure 9:
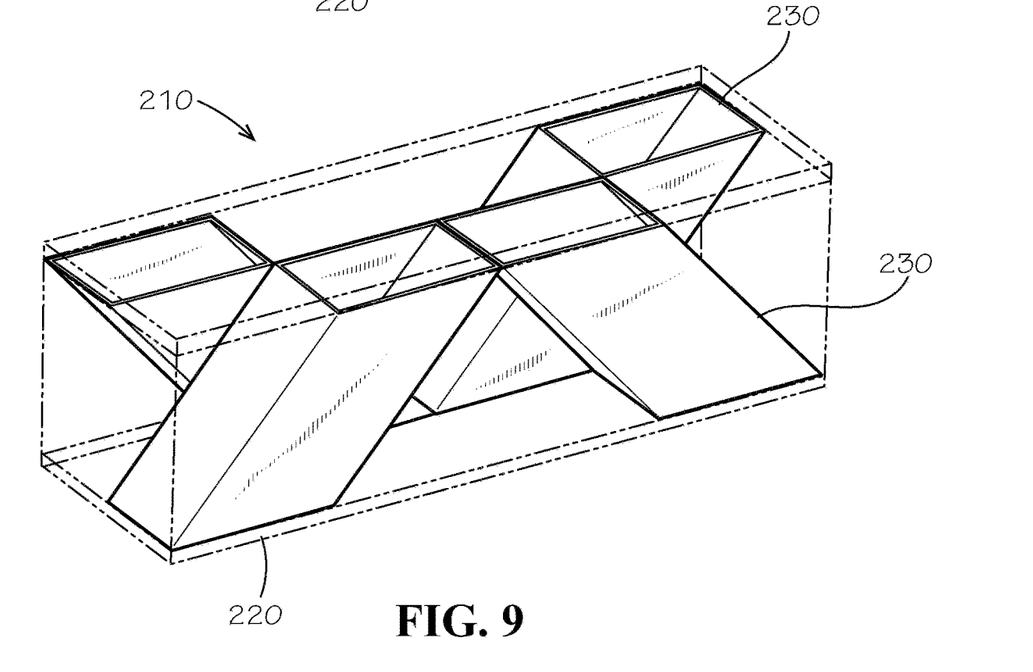
FIG. 9 is a perspective view of a further example of a static mixer that may be used with the hazardous gas detection system.
Figure 10:
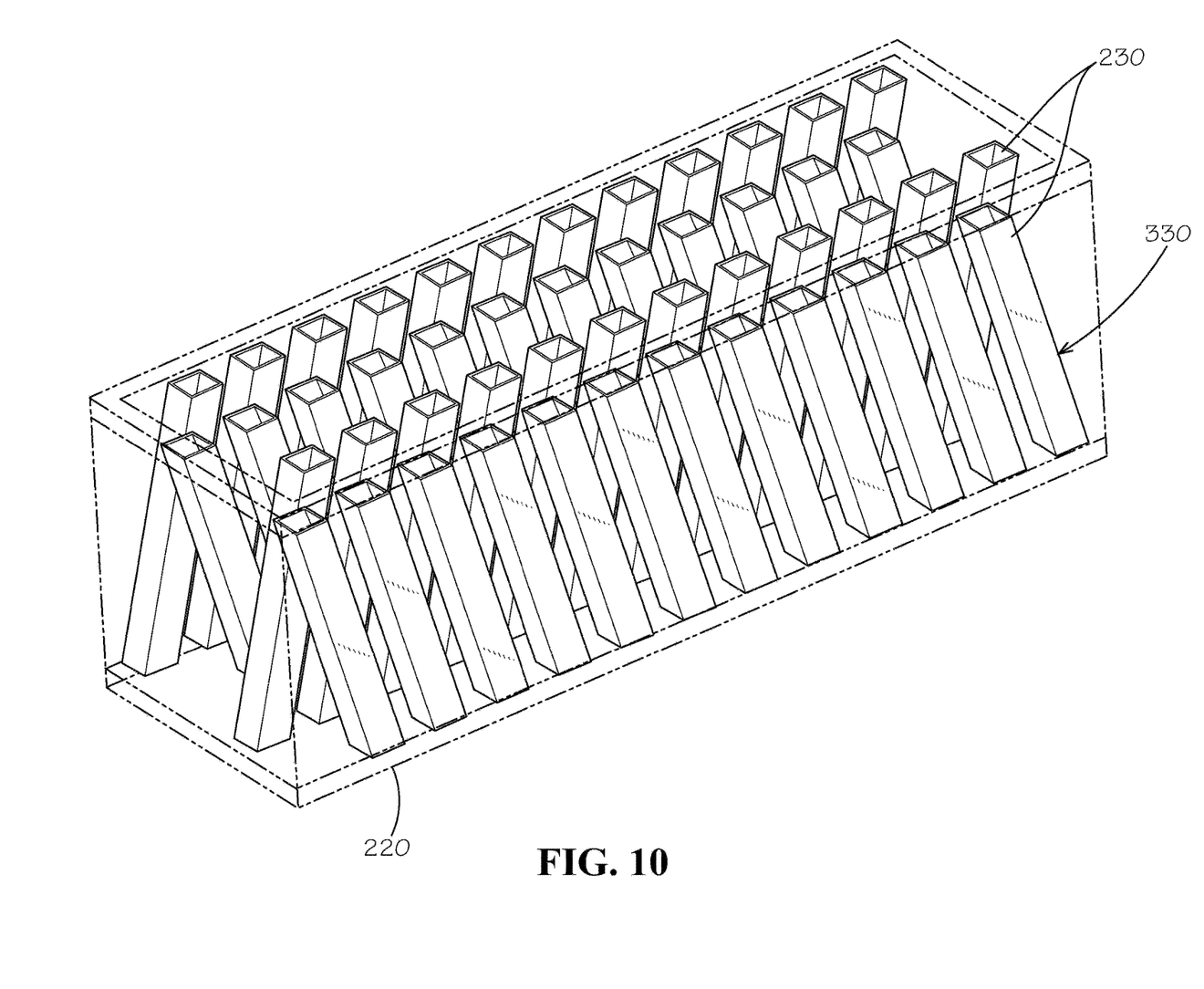
FIG. 10 is a perspective view of a further example of a static mixer that may be used with the hazardous gas detection system.

FIG. 9 shows a further example of a static mixer 210 with a number of angled ducts 230. In this example, the entrance side walls 250 and the exit side walls 260 are positioned about a top of the outer shell 220. The number of ducts 230, the length of the ducts 230, and the angles of the ducts 230 may vary. FIG. 10 shows a static mixer 210 with a number of angled ducts 230 positioned in a number of rows 330 with each row 330 having a varying angle. Other components and other configurations may be used herein.

The static mixers 210 described herein are for the purpose of example only. Many other static mixer designs and configurations may be used herein depending upon, for example, the size of the respective equipment, the desired pressure drop therethrough, and other types of performance goals and parameters.

The static mixers 210 thus achieve a flow of the exhaust air 98 with a uniform leaked fuel gas 95 concentration and temperature at the plane of the sampling tubes 120. Such a uniform concentration and temperature provides more reliable sensor readings regardless of any type of operability/leak scenario. Moreover, the static mixers 210 provide this reliability with an overall lower pressure drop therethrough. Further, such reliability may lead to a reduction in the overall number of sensors require to be used herein. Finally, reducing false alarms and needless shutdowns promotes overall plant usage and efficiency. The static mixers 210 may be original equipment or installed as a retrofit.

It should be apparent that the foregoing relates only to certain embodiments of the present application and the resultant patent. Numerous changes and modifications may be made herein by one of ordinary skill in the art without departing from the general spirit and scope of the invention as defined by the following claims and the equivalents thereof.

Exemplary clauses that may be used to describe the present hazardous gas detection system and method include:
1. A hazardous gas detection system to determine hazardous gas concentrations and temperatures within a flow of exhaust air in an exhaust duct of a gas turbine compartment, comprising: one or more sensors positioned within or in communication with the exhaust duct; and a static mixer positioned upstream of the one or more sensors to promote mixing of the flow of exhaust air.
2. The hazardous gas detection system of the previous clause, wherein the static mixer is positioned within the gas turbine compartment adjacent to the exhaust duct.
3. The hazardous gas detection system of any previous clause, wherein the static mixer is positioned within the exhaust duct adjacent to the gas turbine compartment.
4. The hazardous gas detection system of any previous clause, wherein the exhaust duct comprises an instrumentation duct comprising the one or more sensors; and wherein the static mixer is positioned upstream of the instrumentation duct.
5. The hazardous gas detection system of any previous clause, further comprising one or more sampling tubes positioned within the exhaust duct.
6. The hazardous gas detection system of any previous clause, wherein the one or more sensors comprise hazardous gas sensors in communication with the one or more sampling tubes.

7. The hazardous gas detection system of any previous clause, wherein the one or more sensors comprise thermocouples positioned about the one or more sampling tubes.

8. The hazardous gas detection system of any previous clause, wherein the static mixer comprises an outer shell and a plurality of ducts.

9. The hazardous gas detection system of any previous clause, wherein the plurality of ducts comprises a pair of ducts positioned in a crossed configuration.

10. The hazardous gas detection system of any previous clause, wherein each of the plurality of ducts comprises an entrance wall and an exit wall.

11. The hazardous gas detection system of any previous clause, wherein each of the entrance wall and the exit wall comprises a plurality of apertures therein.

12. The hazardous gas detection system of any previous clause, wherein each of the plurality of ducts comprises a lateral side wall; and wherein the lateral sidewall comprises a plurality of apertures.

13. The hazardous gas detection system of any previous clause, wherein each of the plurality of ducts comprises a splitter plate therein.

14. The hazardous gas detection system of any previous clause, wherein the plurality of ducts comprises a plurality of angled ducts positioned in a plurality of rows.

15. A method of determining a concentration or temperature of a hazardous gas in a flow of exhaust air in an exhaust duct of a gas turbine compartment, the method comprising: pulling the flow of exhaust air into the exhaust duct; positioning a static mixer in the flow of exhaust air; uniformly mixing the hazardous gas within the flow of exhaust air; and sensing the concentration or temperature of the hazardous gas 16. A hazardous gas detection system to determine hazardous gas concentrations and temperatures within a flow of exhaust air in an exhaust duct of a gas turbine compartment, the hazardous gas detection system comprising: one or more gas sensors and one or more temperature sensors positioned within or in communication with the exhaust duct; and a static mixer positioned upstream of the one or more gas sensors and the one or more temperature sensors to promote mixing of the flow of exhaust air.

17. The hazardous gas detection system of the previous clause, wherein the static mixer is positioned within the gas turbine compartment adjacent to the exhaust duct.

18. The hazardous gas detection system of any of clauses 16 or 17, wherein the static mixer is positioned within the exhaust duct adjacent to the gas turbine compartment.

19. The hazardous gas detection system of any of clauses 16, 17, or 18, wherein the exhaust duct comprises an instrumentation duct comprising the one or more gas sensors and the one or more temperature sensors; and wherein the static mixer is positioned upstream of the instrumentation duct.

20. The hazardous gas detection system of any of clauses 16-19, wherein the static mixer comprises an outer shell and a plurality of ducts; and wherein each duct of the plurality of ducts includes one or more walls comprising a plurality of apertures.

What we claim is:

1. A hazardous gas detection system to determine hazardous gas concentrations and temperatures within a flow of exhaust air in an exhaust duct of a gas turbine compartment, comprising:
    one or more sensors positioned within or in communication with the exhaust duct; and
    a static mixer positioned upstream of the one or more sensors to promote mixing of the flow of exhaust air, wherein the static mixer comprises a plurality of ducts and wherein each of the plurality of ducts comprises one or more walls comprising a plurality of apertures.

2. The hazardous gas detection system of claim 1, wherein the static mixer is positioned within the gas turbine compartment adjacent to the exhaust duct.

3. The hazardous gas detection system of claim 1, wherein the static mixer is positioned within the exhaust duct adjacent to the gas turbine compartment.

4. The hazardous gas detection system of claim 1, wherein the exhaust duct comprises an instrumentation duct comprising the one or more sensors and wherein the static mixer is positioned upstream of the instrumentation duct.

5. The hazardous gas detection system of claim 1, further comprising one or more sampling tubes positioned within the exhaust duct.

6. The hazardous gas detection system of claim 5, wherein the one or more sensors comprise hazardous gas sensors in communication with the one or more sampling tubes.

7. The hazardous gas detection system of claim 5, wherein the one or more sensors comprise thermocouples positioned about the one or more sampling tubes.

8. The hazardous gas detection system of claim 1, wherein the plurality of ducts comprises a pair of ducts positioned in a crossed configuration.

9. The hazardous gas detection system of claim 1, wherein the one or more walls comprise an entrance wall and an exit wall.

10. The hazardous gas detection system of claim 9, wherein each of the entrance wall and the exit wall comprises the plurality of apertures therein.

11. The hazardous gas detection system of claim 1, wherein the one or more walls comprise a lateral side wall and wherein the lateral sidewall comprises the plurality of apertures.

12. The hazardous gas detection system of claim 1, wherein each of the plurality of ducts comprises a splitter plate therein.

13. The hazardous gas detection system of claim 1, wherein the plurality of ducts comprises a plurality of angled ducts positioned in a plurality of rows.

14. A method of determining a concentration or temperature of a hazardous gas in a flow of exhaust air in an exhaust duct of a gas turbine compartment, comprising:
    pulling the flow of exhaust air into the exhaust duct;
    positioning a static mixer in the flow of exhaust air, wherein the static mixer comprises a plurality of ducts and wherein each of the plurality of ducts includes one or more walls comprising a plurality of apertures;
    uniformly mixing the hazardous gas within the flow of exhaust air; and
    sensing the concentration or temperature of the hazardous gas.

15. A hazardous gas detection system to determine hazardous gas concentrations and temperatures within a flow of exhaust air in an exhaust duct of a gas turbine compartment, comprising:
- one or more gas sensors and one or more temperature sensors positioned within or in communication with the exhaust duct; and
- a static mixer positioned upstream of the one or more gas sensors and the one or more temperature sensors to promote mixing of the flow of exhaust air;
- wherein the static mixer comprises a plurality of ducts and wherein each of the plurality of ducts includes one or more walls comprising a plurality of apertures.

16. The hazardous gas detection system of claim 15, wherein the static mixer is positioned within the gas turbine compartment adjacent to the exhaust duct.

17. The hazardous gas detection system of claim 15, wherein the static mixer is positioned within the exhaust duct adjacent to the gas turbine compartment.

18. The hazardous gas detection system of claim 15, wherein the exhaust duct comprises an instrumentation duct comprising the one or more gas sensors and the one or more temperature sensors and wherein the static mixer is positioned upstream of the instrumentation duct.

* * * * *